US006555102B1

(12) United States Patent
Hoshino et al.

(10) Patent No.: US 6,555,102 B1
(45) Date of Patent: *Apr. 29, 2003

(54) DEODORANT AND ANTIMICROBIAL COMPOSITIONS

(75) Inventors: Akira Hoshino, Tokyo (JP); Mikio Saji, Tokyo (JP); Kozaburo Hayashi, Tokyo (JP)

(73) Assignee: Dainichiseika Color & Chemicals Mfg. Co., Ltd., Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 09/563,491

(22) Filed: May 3, 2000

(51) Int. Cl.$^7$ .............................. A61L 9/00; A61L 11/00
(52) U.S. Cl. .................. 424/76.1; 424/76.5; 424/76.6; 424/76.7
(58) Field of Search ................ 424/76.1, 76.5, 424/76.6, 76.7

(56) References Cited

U.S. PATENT DOCUMENTS

| | | | |
|---|---|---|---|
| 3,885,961 A | 5/1975 | Kimura et al. ............... 96/1.5 |
| 3,996,142 A | 12/1976 | White et al. ................. 252/8.1 |
| 4,154,618 A | 5/1979 | Burke ......................... 106/27 |
| 4,166,744 A | 9/1979 | Smith .......................... 106/35 |
| 4,226,982 A * | 10/1980 | Blount ....................... 536/101 |
| 4,316,969 A | 2/1982 | Koyama et al. ............. 525/145 |
| 4,454,050 A | 6/1984 | Bertell ....................... 252/42 |
| 4,735,972 A | 4/1988 | Shigematsu et al. ........ 523/102 |
| 4,757,099 A * | 7/1988 | Hoshino et al. ............ 523/102 |
| 4,863,987 A | 9/1989 | Hoshino et al. ............ 524/293 |
| 4,880,852 A | 11/1989 | Hoshino et al. ............ 523/102 |
| 4,931,360 A | 6/1990 | Hoshino et al. ............ 428/328 |
| 5,063,256 A | 11/1991 | Hoshino et al. ............ 523/102 |
| 5,480,643 A * | 1/1996 | Donovan et al. ........... 424/409 |
| 6,278,007 B1 * | 8/2001 | Inaoka et al. .............. 554/126 |

FOREIGN PATENT DOCUMENTS

| | | | |
|---|---|---|---|
| JP | 01254232 | * | 10/1989 |
| JP | 11293034 | * | 10/1999 |
| JP | 20001434 | * | 5/2000 |
| WO | 94/13765 | * | 6/1994 |

OTHER PUBLICATIONS

William H. Brown, Introduction to Organic Chemistry, "Amines," Chapter 10, 1997, pp. 277–299.

\* cited by examiner

Primary Examiner—Thurman K. Page
Assistant Examiner—S. Tran
(74) Attorney, Agent, or Firm—Oblon, Spivak, McClelland, Maier & Neustadt, P.C.

(57) ABSTRACT

A deodorant and antimicrobial composition comprises an oxide or hydroxide of an alkaline earth metal, hydrated silica, and a cationic surfactant. A deodorant and antimicrobial resin composition can be obtained using the deodorant and antimicrobial composition and a thermoplastic resin. This deodorant and antimicrobial resin composition can be molded or otherwise formed.

7 Claims, No Drawings

DEODORANT AND ANTIMICROBIAL
COMPOSITIONS

BACKGROUND OF THE INVENTION a) Field of the Invention

This invention relates to deodorant and antimicrobial compositions, deodorant and antimicrobial resin compositions making use of the deodorant and antimicrobial compositions, and formed deodorant and antimicrobial resin products obtained by molding or otherwise forming the resin compositions. Described more specifically, the present invention is concerned with deodorant and antimicrobial compositions useful for imparting deodorizing power and antimicrobial activity to various base materials such as paints, synthetic fibers, synthetic resins and paper, deodorant and antimicrobial resin compositions making use of the deodorant and antimicrobial compositions, and formed deodorant and antimicrobial resin products obtained by molding or otherwise forming the resin compositions.

b) Description of the Related Art

Numerous deodorant and antimicrobial agents have been used to date in various fields. In particular, a variety of products such as films, wall paper, decorated plywood, building materials, fibers, nonwoven fabrics and clothing are required to remain free of offensive odor, bacteria, fungi and the like. If offensive odor, bacteria, fungi or the like occurs, a need often arises for its removal.

In recent years, there is an ever-increasing demand for the amenity of living space. In view of the crowding of houses due to urbanization and also of the living environment of a closed house or building structure constructed of concrete and aluminum sash windows, it has become an indispensable condition for clean-environment life that visual and olfactory unpleasant feeling and hygienically unpleasant feeling, such as microbial contamination, be removed.

Described specifically, formaldehyde-linked health disturbances have posed problems in recent years. The odor of formaldehyde has already become a social problem as "sick house syndrome" in a living environment of a closed house structure, especially in a newly-built house. This problem is attributed to formaldehyde given off from newly-developed building materials. Various products—such as wall paper, decorated plywood, building materials, fibers, nonwoven fabrics, clothing, sundries and films—are hence required to have a function to remove the odor of formaldehyde given off as described above. Further, from the view point of hygine such as prevention of microbial contamination, such products are also required to be equipped with an antimicrobial and antifungal function.

SUMMARY OF THE INVENTION

An object of the present invention is, therefore, to provide a deodorant and antimicrobial composition which can impart excellent deodorizing power and antimicrobial activity to various materials.

The above-described object can be achieved by the present invention to be described subsequently herein. Namely, the present invention provides a deodorant and antimicrobial composition comprising an oxide or hydroxide of an alkaline earth metal, hydrated silica and a cationic surfactant; a deodorant and antimicrobial resin composition making use of the deodorant and antimicrobial composition, and also a formed deodorant and antimicrobial resin product obtained by molding or otherwise forming the resin composition.

The deodorant and antimicrobial composition, deodorant and antimicrobial resin composition and formed deodorant and antimicrobial resin product according to the present invention are effective for the deodorization of acetoaldehyde odor, formaldehyde odor, acetic acid odor and the like out of various offensive odors. Further, the deodorant and antimicrobial composition, deodorant and antimicrobial resin composition and formed deodorant and antimicrobial resin product according to the present invention are also excellent in antimicrobial activity.

In addition, the deodorant and antimicrobial composition, deodorant and antimicrobial resin composition and formed deodorant and antimicrobial resin product according to the present invention can impart excellent deodorizing power and antimicrobial activity to various articles.

DETAILED DESCRIPTION OF THE INVENTION AND PREFERRED EMBODIMENTS

The present invention will next be described more specifically based on preferred embodiments.

The deodorant and antimicrobial composition according to the present invention comprises, in combination, an oxide or hydroxide of an alkaline earth metal, hydrated silica, and a cationic surfactant. Illustrative of the alkaline earth metal oxide or hydroxide are the oxides and hydroxides of barium, calcium, magnesium and the like, with magnesium hydroxide being particularly effective.

This alkaline earth metal oxide or hydroxide may be used preferably in such a proportion that, when the total amount of the deodorant and antimicrobial composition is supposed to be 100 parts by weight, it amounts to 80 to 40 parts by weight. A proportion of the alkaline earth metal oxide or hydroxide smaller than the above range leads to insufficient performance in that conversion of aldehydes, especially formaldehyde into formose becomes slower. On the other hand, a proportion of the alkaline earth metal oxide or hydroxide greater than the above range also leads to insufficient performance in that the proportion of a substance adapted to undergo an addition reaction with formaldehyde for the removal of formaldehyde, that is, the cationic surfactant in the composition decreases, thereby lowering the deodorizing reaction velocity of aldehydes and resulting in insufficient fast-acting property.

The hydrated silica for use in the present invention is represented by the empirical formula $SiO_2 \cdot nH_2O$, and is in the form of secondary particles formed as a result of flocculation of fine silica particles having many silanol groups on surfaces thereof. Such hydrated silica is a flocculate of ultrafine particles of hydrated silica, which is available from a reaction of sodium silicate with a mineral acid, and contains a number of voids between particles. These voids effectively act for the adsorption of various offensive odor components such as formaldehyde.

Such hydrated silica is available, for example, from Mizusawa Industrial Chemicals, Inc., Tokyo, Japan under the trade names of "P-801", "P-802", "P-526", "P-527", "P-603", "P-604", "P-554A", "P-73", "P-78A", "P-78D", "P-78F", "P-707", "P-740", "P-752", "P-50", "P-766", "C-1", "S-0", "NP-8", "P-802Y", "P-832", "P-87", "P-363", "C-002", "C-402" and "C-484", all of which are usable in the present invention.

The above-described hydrated silica may be used preferably in such a proportion that, when the total amount of the deodorant and antimicrobial composition is supposed to be 100 parts by weight, it amounts to 50 to 10 parts by weight.

A proportion of the hydrated silica smaller than the above range leads to insufficient performance in that the deodorizing reaction velocity of aldehydes becomes slower, resulting in insufficient fast-acting property. On the other hand, a proportion of the hydrated silica greater than the above range also leads to insufficient performance in that, when the deodorant and antimicrobial composition according to the present invention is kneaded with a resin, the flowability of the resin is rendered poor.

As the cationic surfactant for use in the present invention, one represented by the empirical formula HO—R—NHCH$_2$CH$_2$OH in which R is a C$_{12}$–C$_{14}$ alkylene group is preferred. The cationic surfactant reacts with an aldehyde group of formaldehyde or the like, thereby converting such an aldehyde compound into an odorless compound. Such cationic surfactants are available from Miyoshi Oil & Fat Co., Ltd., Tokyo, Japan under the trade names of "Miyocol 368E" "Miyocol QX-33N", "Duspar 125B", "Duspar 125BN", "Duspar 125BS" and "Duspar 1400B", all of which are usable in the present invention.

The above-described cationic surfactants can be used either singly or in combination. They, however, include some compounds which, when mixed to produce deodorant and antimicrobial compositions, may not be sufficient in dispersibility, stability, thermal stability, light fastness, processability and/or the like. Upon using the deodorant and antimicrobial composition of this invention for various applications, heat resistance is also important in connection with processability. From this viewpoint, "Duspar 125B" and "Duspar 125BN" are particularly preferred.

The above-described cationic surfactant may be used preferably in such a proportion that, when the total amount of the deodorant and antimicrobial composition is supposed to be 100 parts by weight, it amounts to 0.1 to 30 parts by weight. If the cationic surfactant is used in a proportion smaller than the above range, the resulting composition is insufficient in performance in that the velocity of deodorizing reaction with aldehydes becomes slower and the antimicrobial activity is insufficient. If the cationic surfactant is used in a proportion greater than the above range, on the other hand, the resulting composition itself is no longer provided with powdery property and its handling is deteriorated.

The deodorant and antimicrobial composition which comprises such components as described above can be obtained by simply mixing the individual components together, and can be used for various applications like conventional deodorant and antimicrobial agents.

When it is desired to impart deodorizing power and antimicrobial activity to a variety of formed resin products by using the above-described deodorant and antimicrobial composition of the present invention, the deodorant and antimicrobial composition can be mixed with resins into deodorant and antimicrobial resin compositions.

Examples of the resin for use in the present invention can include synthetic or modified thermoplastic resins, for example, polyolefin resins such as polyethylene and polypropylene, polyvinyl chloride, vinylon, polystyrene, polyamides, polyesters, and cellulose acetate, which have been used for manyvyears in various molded or otherwise formed products, for example, formolding or otherwise forming plastic films, plastic sheets, plastic containers, fibers and the like. These thermoplastic resins are all readily available from the market for use in the present invention, and may be either in a solid form or in a liquid form such as a paste form.

The deodorant and antimicrobial resin composition according to the present invention comprises, as essential components, two components, that is, the above-described resin and the above-described deodorant and antimicrobial composition. As their mixing ratio, 99.9 to 50 parts by weight of the resin and 0.1 to 50 parts by weight of the deodorant and antimicrobial composition, preferably 99.0 to 80 parts by weight of the resin and 1.0 to 20 parts by weight of the deodorant and antimicrobial composition can be mixed. To the resin composition according to the present invention, a variety of conventionally-known other additives for resin, for example, colorants, fillers, extender pigments, plasticizers, stabilizers, ultraviolet absorbers and the like can be added optionally as needed.

The deodorant and antimicrobial resin composition according to the present invention can be obtained by simply mixing the above-described components together or by further melting, kneading and granulating the mixture into pellets or the like. It can also be in the form of a master batch which contains a deodorant and antimicrobial component at such a high concentration (for example, a concentration of from 10 to 50 wt. %) as permitting subsequent dilution with natural (i.e., additive-free) thermoplastic-resin.

The above-described deodorant and antimicrobial resin composition is useful for the production of a formed deodorant ,and antimicrobial resin product. Examples of the formed deodorant and antimicrobial resin product of the present invention can include those obtained by molding or otherwise forming the deodorant and antimicrobial resin composition into various shapes, for example, wrapping materials made of plastic films or sheets and containers of desired shapes obtained by molding or otherwise forming the deodorant and antimicrobial resin composition by various processes.

The forming or molding of such films, sheets, containers or the like can be performed by a conventionally-known inflation extruder, press, calender, extruder, spinning machine, blow molding machine, injection molding machine, vacuum forming machine or the like by using conventionally-known various conditions as are, so that the formed deodorant and antimicrobial resin product according to the present invention can be obtained with ease.

The present invention will next be described more specifically based on describing examples and a comparative example, in which all designations of "part or parts" and are on weight basis.

EXAMPLE 1

With 97 parts of low-density polyethylene, 3 parts of a mixture (a deodorant and antimicrobial composition according to the present invention) consisting of magnesium hydroxide, hydrated silica ("P-766", trade name) and a cationic surfactant ("Duspar 125B", trade name) at a weight ratio of 6:3:1 were combined. The resulting mixture was processed in a mixer and then kneaded in a 40-mm extruder (L/D: 28, C.R.: 3.1, Dulmage screw, cylinder temperature: 130° C., screw speed: 70 rpm), whereby a pellet-shaped, deodorant and antimicrobial resin composition according to the present invention was obtained.

The deodorant and antimicrobial resin composition was then charged in an inflation extruder (30-mm extruder, inflation die of 50 mm in inner diameter, cylinder temperature: 140° C., screw speed: 60 rpm) and was subjected to blow-film extrusion. As a result, a polyethylene film of 50 μm was obtained.

EXAMPLE 2

A plastic film according to the present invention was obtained in a similar manner as in Example 1 except that a deodorant and antimicrobial composition and a deodorant and antimicrobial resin composition were prepared using the following components:

| | |
|---|---|
| Low-density polyethylene | 95 parts |
| 5:3:2, by weight, mixture of magnesium hydroxide/ hydrated silica ("P-707", trade name)/ cationic surfactant ("Duspar 125B", trade name) | 5 parts |

EXAMPLE 3

A plastic film according to the present invention was obtained in a similar manner as in Example 1 except that a deodorant and antimicrobial composition and a deodorant and antimicrobial resin composition were prepared using the following components:

| | |
|---|---|
| Polypropylene | 97 parts |
| 5:4:1, by weight, mixture of calcium hydroxide/ hydrated silica ("P-740", trade name)/ cationic surfactant ("Duspar 125B", trade name) | 3 parts |

EXAMPLE 4

A plastic film according to the present invention was obtained in a similar manner as in Example 1 except that a deodorant and antimicrobial composition and a deodorant and antimicrobial resin composition were prepared using the following components:

| | |
|---|---|
| Polystyrene | 97 parts |
| 4:4:2, by weight, mixture of calcium hydroxide/ hydrated silica ("P-752", trade name)/ cationic surfactant ("Duspar 125B", trade name) | 3 parts |

EXAMPLE 5

Seventy (70) parts of polypropylene and 30 parts of a deodorant and antimicrobial composition [a mixture consisting of magnesiumhydroxide, hydratedsilicate ("P-766", tradename) and a cationic surfactant ("Duspar 125B", trade name) at a weight ratio of 6:3:1] were combined. The resulting mixture was processed for 2 minutes at a rotational speed of 1,500 rpm in a Henschel mixer, and was then kneaded in a 40-mm extruder (L/D: 28, C.R.: 3.1, Dulmage screw, cylinder temperature: 200 to 215° C., screw speed: 90 rpm), whereby a pellet-shaped deodorant and antimicrobial resin composition was obtained. The resin composition was extended tenfold with the natural resin (polypropylene). By a spinning machine, the thus-extended resin composition was spun at 200 to 215° C., followed by stretching into 15-denier filaments. End breakages occurred neither in the course of the spinning nor during the stretching.

EXAMPLE 6

Seventy (70) parts of a polyester and 30 parts of a deodorant and antimicrobial composition [a mixture consisting of magnesium oxide, hydrated silicate ("P-766", trade name) and a cationic surfactant ("Duspar 125B", trade name) at a weight ratio of 5:4:1] were combined. The resulting mixture was processed for 2 minutes at a rotational speed of 1,500 rpm in a Henschel mixer, and was then kneaded in a 40-mm extruder (L/D: 28, C.R.:3.1, Dulmage screw, cylinder temperature: 270 to 280° C., screw speed: 90 rpm), whereby a pellet-shaped deodorant and antimicrobial resin composition was obtained. The resin composition was extended tenfold with the natural resin (polyester). By a spinning machine, the thus-extended resin composition was spun at 280 to 290° C., followed by stretching into 15-denier filaments. End breakages occurred neither in the course of the spinning nor during the stretching.

Evaluation

Deodorizing and antimicrobial effects of the various formed products obtained in Examples 1–6 were investigated by the following testing methods, respectively. The results are summarized in Table 1 to Table 5.

[Deodorizing Performance Testing ethods]

(Acetic-acid Deodorization Test)

In a 300-mL Erlenmeyer flask, a 2% aqueous solution of acetic acid (2.5 μL) was placed, followed by the addition of a sample. The flask was left over at 25° C., and subsequent to an elapse of a predetermined time, the concentration of acetic acid still remaining in the flask was measured using a Kitagawa gas detector. The results are presented in Table 1.

(Formaldehyde Deodorization Test)

In a 300-mL Erlenmeyer flask, a 3.5% aqueous solution of formaldehyde (1 μL) was placed, followed by the addition of a sample. The flask was left over at 25° C., and subsequent to an elapse of a predetermined time, the concentration of formaldehyde still remaining in the flask was measured using the Kitagawa gas detector. The results are presented in Table 2.

(Acetoaldehyde Deodorization Test)

In a 300-mL Erlenmeyer flask, a 2.5% aqueous solution of acetoaldehyde (1 μL) was placed, followed by the addition of a sample. The flask was left over at 25° C., and subsequent to an elapse of a predetermined time, the concentration of acetoaldehyde still remaining in the flask was measured using the Kitagawa gas detector. The results are presented in Table 3.

TABLE 1

Results of Acetic Acid Deodorization Test

| | Concentration of acetic acid (ppm) | | | |
|---|---|---|---|---|
| | 5 min later | 30 min later | 120 min later | Test sample |
| Blank | 45 | 45 | 45 | Film piece (50 mm × 200 mm) |
| Example 1 | 2 | Not detected | Not detected | Film piece (50 mm × 200 mm) |
| Example 2 | 3 | Not detected | Not detected | Film piece (50 mm × 200 mm) |
| Example 3 | 1 | Trace | Not detected | Film piece (50 mm × 200 mm) |
| Example 4 | 2 | Not detected | Not detected | Film piece (50 mm × 200 mm) |

TABLE 1-continued

Results of Acetic Acid Deodorization Test

Concentration of acetic acid (ppm)

| | 5 min later | 30 min later | 120 min later | Test sample |
|---|---|---|---|---|
| Example 5 | Not detected | Not detected | Not detected | Filaments 0.2 g |
| Example 6 | Not detected | Not detected | Not detected | Filaments 0.2 g |
| Comp. Ex. | 6 | 3 | Trace | Filaments 0.2 g |

In the blank, a polyethylene film prepared in a similar manner as in Example 1 except that the deodorant and antimicrobial composition was not used was used as a test sample.
In the comparative example, filaments prepared in a similar manner as in Example 5 except that the deodorant and antimicrobial composition was not added with the cationic surfactant was used as a test sample.
These footnotes will apply equally to Table 2 and Table 3.

TABLE 2

Results of Formaldehyde Deodorization Test

Concentration of formaldehyde (ppm)

| | 5 min later | 30 min later | 120 min later | Test sample |
|---|---|---|---|---|
| Blank | 105 | 105 | 105 | Film piece (50 mm × 200 mm) |
| Example 1 | 10 | 6 | 2 | Film piece (50 mm × 200 mm) |
| Example 2 | 10 | 7 | 2 | Film piece (50 mm × 200 mm) |
| Example 3 | 12 | 8 | 3 | Film piece (50 mm × 200 mm) |
| Example 4 | 10 | 5 | 1 | Film piece (50 mm × 200 mm) |
| Example 5 | Not detected | Not detected | Not detected | Filaments 0.2 g |
| Example 6 | Not detected | Not detected | Not detected | Filaments 0.2 g |
| Comp. Ex. | 15 | 10 | 5 | Filaments 0.2 g |

TABLE 3

Results of Acetoaldehyde Deodorization Test

Concentration of acetoaldehyde (ppm)

| | 5 min later | 30 min later | 120 min later | Test sample |
|---|---|---|---|---|
| Blank | 35 | 35 | 35 | Film piece (50 mm × 200 mm) |
| Example 1 | 10 | 6 | 1 | Film piece (50 mm × 200 mm) |
| Example 2 | 10 | 7 | 2 | Film piece (50 mm × 200 mm) |
| Example 3 | 9 | 4 | 1 | Film piece (50 mm × 200 mm) |
| Example 4 | 5 | 3 | Trace | Film piece (50 mm × 200 mm) |
| Example 5 | 3 | Trace | Not detected | Filaments 0.2 g |
| Example 6 | 1 | Not detected | Not detected | Filaments 0.2 g |
| Comp. Ex. | 15 | 10 | 10 | Filaments 0.2 g |

[Antimicrobial test]

Tested Bacteria Strains

Gram-negative bacteria: *Escherichia coli* IFO 3972
Gram-positive bacteria: *Staphylococcus aureus* IFO 12732

Testing Method

Preculture: Cultured at 37° C. under shaking on nutrient broth liquid medium (*E. coli*: 16 hours, *S. aureus*: 12 hours).
Antimicrobial test: A sterilized sample (about 50×50 mm; 0.05 g in the case of filaments) was dried and then placed in a sterilized Petri dish. On the side, the above-described precultures were diluted to prepare the inocula shown in Table 4 an Table 5, respectively. In the case of the preculture of *E. coli*, the inoculum was prepared by diluting the preculture with a solution such that the viable cell count per mL was adjusted to $3.1 \times 10^5$. The solution had been prepared by diluting the nutrient broth liquid medium with phosphate buffer (pH 7.2) such that the concentrations of its nutrients were lowered to 1/500. In the case of the preculture of *S. aureus*, on the other hand, the inoculum was prepared by diluting the preculture with a solution such that the viable cell count per mL was adjusted to $8.5 \times 10^4$. The solution had been prepared by diluting the nutrient broth liquid medium with phosphate buffer (pH 7.2) such that the concentrations of its nutrients were lowered to 1/50. Concerning each cell strain, the inoculum the viable cell count of which had been adjusted as described above was inoculated to a surface of each sample at four diagonal corners of the sample and also at a center of the sample in an amount of 0.1 mL per location, that is, in a total amount of 0.5 mL. After incubation at 30±1° C. and a relative humidity of 90% or higher for 24 hours, cells were washed out with phosphate buffer (4.5 mL). By the pour plate method, the viable cell count of the test solution was determined using nutrient agar. Further, as a control, a Petri dish with the inoculum alone dropped therein was also tested.

TABLE 4

Results of Antimicrobial Test on *E. coli*

| Sample | Viable cell count (cells/mL) | Inhibition rate (%) |
| --- | --- | --- |
| Inoculum (initial viable cell count) | $3.1 \times 10^5$ | — |
| Control | $1.9 \times 10^5$ | — |
| Example 1 | <10 | >99.99 |
| Example 2 | <10 | >99.99 |
| Example 3 | <10 | >99.99 |
| Example 4 | <10 | >99.99 |
| Example 5 | <10 | >99.99 |
| Example 6 | <10 | >99.99 |
| Comparative Example | $7.9 \times 10^6$ | 0 |

In the control, the inoculum was left over without addition of any sample to the Petri.
In the comparative example, a film prepared in a similar manner as in Example 1 except that the deodorant and antimicrobial composition was not added with the cationic surfactant was used as a test sample.
These footnotes will apply equally to Table 5.

TABLE 5

Results of Antimicrobial Test on *S. aureus*

| Sample | Viable cell count (cells/mL) | Inhibition rate (%) |
| --- | --- | --- |
| Inoculum (initial viable cell count) | $8.5 \times 10^4$ | — |
| Control | $6.7 \times 10^4$ | — |
| Example 1 | <10 | >99.99 |
| Example 2 | <10 | >99.99 |
| Example 3 | <10 | >99.99 |
| Example 4 | <10 | >99.99 |
| Example 5 | <10 | >99.99 |
| Example 6 | <10 | >99.99 |
| Comparative Example | $6.8 \times 10^4$ | 0 |

EXAMPLE 7

The pellet-shaped deodorant and antimicrobial granules (100 g) obtained in Example 1 were filled in a filter pocket of a vacuum cleaner ("CV-C45"; trade name; manufactured by Hitachi, Ltd.), and in a room (temperature: 26° C., humidity: 75%), walls and a floor were swept clean by the vacuum cleaner. The concentration of formaldehyde in the room dropped from 0.279 ppm to 0.003 ppm (percent removal of formaldehyde: 80%), and in a closet, the concentration of formaldehyde dropped from 0.467 ppm to 0.003 ppm (percent removal of formaldehyde: 90%).

What is claimed is:

1. A composition comprising:
   an oxide or hydroxide of an alkaline earth metal;
   hydrated silica; and
   a cationic surfactant represented by the formula $HO-R-NHCH_2CH_2OH$ in which R is a $C_{12}-C_{14}$ alkylene group.

2. A composition according to claim 1, wherein, when a total amount of said composition is 100 parts by weight, said oxide or hydroxide of an alkaline earth metal amounts to 80 to 40 parts by weight, said hydrated silica amounts to 50 to 10 parts by weight, and said cationic surfactant amounts to 0.1 to 30 parts by weight.

3. A composition according to claim 1, wherein said oxide or hydroxide of said alkaline earth metal is magnesium hydroxide.

4. The composition as claimed in claim 1, further comprising a thermoplastic resin.

5. A composition as claimed in claim 4, comprising 99.9 to 50 parts by weight of said thermoplastic resin based on 100 parts of said composition.

6. A composition according to claim 3, further comprising a thermoplastic resin.

7. A composition according to claim 1, further comprising a thermoplastic resin, wherein said composition comprises 99.9 to 50 parts by weight of a thermoplastic resin, 40 to 20 parts by weight of said oxide or hydroxide of an alkaline earth metal, 25 to 5 parts by weight of said hydrated silica and 0.05 to 15 parts by weight of said cationic surfactant.

\* \* \* \* \*